US007745682B2

(12) United States Patent
Sigurjonsson et al.

(10) Patent No.: US 7,745,682 B2
(45) Date of Patent: Jun. 29, 2010

(54) WOUND DRESSING AND METHOD FOR MANUFACTURING THE SAME

(75) Inventors: Gudmundur Fertram Sigurjonsson, Reykjavik (IS); Thordur M. Elefsen, Mosfellsbaer (IS); Palmar I. Gudnason, Reykjavik (IS)

(73) Assignee: Ossur hf, Reykjavik (IS)

( * ) Notice: Subject to any disclaimer, the term of this patent is extended or adjusted under 35 U.S.C. 154(b) by 58 days.

(21) Appl. No.: 12/216,386

(22) Filed: Jul. 3, 2008

(65) Prior Publication Data

US 2008/0269660 A1      Oct. 30, 2008

Related U.S. Application Data

(62) Division of application No. 10/924,861, filed on Aug. 25, 2004, now Pat. No. 7,396,975.

(60) Provisional application No. 60/518,317, filed on Nov. 10, 2003, provisional application No. 60/503,546, filed on Sep. 17, 2003, provisional application No. 60/543,401, filed on Feb. 11, 2004.

(51) Int. Cl.
*A61F 13/00* (2006.01)
*A61F 15/00* (2006.01)
*A61F 13/02* (2006.01)

(52) U.S. Cl. .............. 602/56; 602/41; 602/42; 602/43; 602/52; 602/54; 602/55; 128/888; 604/304; 604/307

(58) Field of Classification Search ............. 602/41–59; 128/888–894; 604/304–308
See application file for complete search history.

(56) References Cited

U.S. PATENT DOCUMENTS

| 2,649,088 | A | 8/1953 | Sigg |
| 2,764,976 | A | 10/1956 | Skiles |
| 3,006,338 | A | 10/1961 | Davies |
| 3,042,549 | A | 7/1962 | Arnold |
| 3,113,568 | A | 12/1963 | Robins |
| 3,156,242 | A | 11/1964 | Crowe, Jr. |
| 3,292,619 | A | 12/1966 | Egler |
| 3,307,545 | A | 3/1967 | Surowitz |

(Continued)

FOREIGN PATENT DOCUMENTS

CA          724612         12/1965

(Continued)

OTHER PUBLICATIONS

Molnlycke Healt Care's Business Area Wound Care Global, Mepilex.

(Continued)

*Primary Examiner*—Patricia M Bianco
*Assistant Examiner*—Brandon Jackson
(74) *Attorney, Agent, or Firm*—Bacon & Thomas, PLLC

(57) ABSTRACT

A wound dressing defining skin facing areas having different degrees of skin adherence. The dressing comprises a backing layer defining a center portion and a border portion surrounding the center portion. A carrier layer is secured to the border portion of the backing layer within the border portion and includes a first skin adherent facing layer. An absorbent core is connected to a surface of the backing layer within the center portion and a second skin adherent facing layer is disposed along a surface of the absorbent core. The first facing layer has greater skin adhesive properties than the second facing layer.

5 Claims, 8 Drawing Sheets

U.S. PATENT DOCUMENTS

| | | |
|---|---|---|
| 3,645,835 A | 2/1972 | Hodgson |
| 3,678,933 A | 7/1972 | Moore et al. |
| 3,814,101 A | 6/1974 | Kozak |
| 3,927,669 A | 12/1975 | Glatt |
| 3,972,328 A | 8/1976 | Chen |
| 4,034,751 A | 7/1977 | Hung |
| 4,055,180 A | 10/1977 | Karami |
| 4,175,557 A | 11/1979 | Hung |
| 4,212,296 A | 7/1980 | Schaar |
| 4,360,021 A | 11/1982 | Stima |
| 4,373,519 A | 2/1983 | Errede et al. |
| 4,408,996 A | 10/1983 | Baldwin |
| 4,538,603 A | 9/1985 | Pawelchak et al. |
| 4,560,372 A | 12/1985 | Pieniak |
| 4,603,076 A | 7/1986 | Bowditch et al. |
| 4,614,183 A | 9/1986 | McCracken et al. |
| 4,635,624 A | 1/1987 | Gilman |
| 4,655,210 A | 4/1987 | Edenbaum et al. |
| 4,657,006 A | 4/1987 | Rawlings et al. |
| 4,661,099 A | 4/1987 | von Bittera |
| 4,664,106 A | 5/1987 | Snedeker |
| 4,684,557 A | 8/1987 | Pennace |
| 4,690,683 A | 9/1987 | Chien |
| 4,699,146 A | 10/1987 | Sieverding |
| 4,733,659 A | 3/1988 | Edenbaum et al. |
| 4,738,257 A | 4/1988 | Meyer et al. |
| 4,750,482 A | 6/1988 | Sieverding |
| 4,753,231 A | 6/1988 | Lang et al. |
| 4,762,680 A | 8/1988 | Pennace |
| 4,773,408 A | 9/1988 | Cilento |
| 4,838,253 A | 6/1989 | Brassington et al. |
| 4,846,164 A | 7/1989 | Martz |
| 4,860,737 A | 8/1989 | Lang et al. |
| 4,867,748 A | 9/1989 | Samuelsen |
| 4,906,240 A | 3/1990 | Reed et al. |
| 4,921,704 A | 5/1990 | Fabo |
| 4,950,148 A | 8/1990 | Nakanishi |
| 4,960,477 A | 10/1990 | Mesek |
| 4,977,892 A | 12/1990 | Ewall |
| 4,985,277 A | 1/1991 | Shimizu et al. |
| 4,991,574 A | 2/1991 | Pocknell |
| 4,995,382 A | 2/1991 | Lang et al. |
| 5,010,883 A | 4/1991 | Rawlings et al. |
| 5,074,944 A | 12/1991 | Trenka |
| 5,088,483 A | 2/1992 | Heinecke |
| 5,147,338 A | 9/1992 | Lang et al. |
| 5,160,328 A | 11/1992 | Cartmell et al. |
| 5,167,613 A | 12/1992 | Karami et al. |
| 5,244,457 A | 9/1993 | Karami et al. |
| 5,279,890 A | 1/1994 | Ikeno |
| 5,322,729 A | 6/1994 | Heeter |
| 5,340,363 A | 8/1994 | Fabo |
| 5,352,508 A | 10/1994 | Cheong |
| 5,362,508 A | 11/1994 | Wheeler |
| 5,395,305 A | 3/1995 | Koide et al. |
| 5,409,472 A | 4/1995 | Rawlings et al. |
| 5,445,604 A | 8/1995 | Lang |
| 5,486,158 A | 1/1996 | Samuelsen |
| 5,489,262 A | 2/1996 | Cartmell et al. |
| 5,512,041 A | 4/1996 | Bogart |
| 5,540,922 A | 7/1996 | Fabo |
| 5,556,375 A | 9/1996 | Ewall |
| 5,571,529 A | 11/1996 | Cheong |
| 5,591,820 A | 1/1997 | Kydonieus et al. |
| 5,593,395 A | 1/1997 | Martz |
| 5,603,946 A | 2/1997 | Constantine |
| 5,607,388 A | 3/1997 | Ewall |
| 5,629,014 A | 5/1997 | Kwiatek et al. |
| 5,633,007 A | 5/1997 | Webb et al. |
| 5,635,201 A | 6/1997 | Fabo |
| 5,653,699 A | 8/1997 | Reed et al. |
| 5,681,579 A | 10/1997 | Freeman |
| 5,738,642 A | 4/1998 | Heinecke |
| 5,759,560 A | 6/1998 | Dillon |
| 5,782,787 A | 7/1998 | Webster |
| 5,847,003 A | 12/1998 | Ptchelintsev et al. |
| 5,891,076 A | 4/1999 | Fabo |
| 5,914,125 A | 6/1999 | Andrews et al. |
| 5,919,476 A | 7/1999 | Fischer |
| 5,925,439 A | 7/1999 | Haubach |
| 5,941,840 A | 8/1999 | Court et al. |
| 5,942,332 A | 8/1999 | Nakamura |
| 5,973,221 A | 10/1999 | Collyer et al. |
| 5,981,822 A | 11/1999 | Addison |
| 6,040,492 A | 3/2000 | Lindquist et al. |
| 6,051,317 A | 4/2000 | Brueggemann et al. |
| 6,051,747 A | 4/2000 | Lindqvist et al. |
| 6,066,773 A | 5/2000 | Freeman |
| 6,103,369 A | 8/2000 | Lucast et al. |
| 6,107,536 A | 8/2000 | Dadinis |
| 6,136,039 A | 10/2000 | Kristonsson et al. |
| 6,149,614 A | 11/2000 | Dunshee et al. |
| 6,200,195 B1 | 3/2001 | Furuno |
| 6,207,875 B1 | 3/2001 | Lindqvist et al. |
| 6,242,665 B1 | 6/2001 | Malowaniec |
| 6,291,050 B1 | 9/2001 | Cree |
| 6,320,093 B1 | 11/2001 | Augustine et al. |
| 6,333,093 B1 | 12/2001 | Burrell |
| 6,420,622 B1 | 7/2002 | Johnston |
| 6,461,467 B2 * | 10/2002 | Blatchford et al. ......... 156/230 |
| 6,472,581 B1 | 10/2002 | Muramatsu |
| 6,479,724 B1 | 11/2002 | Areskoug et al. |
| 6,552,244 B1 | 4/2003 | Jacques et al. |
| 6,559,351 B1 | 5/2003 | Eakin |
| 6,566,575 B1 | 5/2003 | Stickels et al. |
| 6,566,576 B1 | 5/2003 | Komerska et al. |
| 6,566,577 B1 | 5/2003 | Addison et al. |
| 6,600,085 B2 | 7/2003 | Sun et al. |
| 6,610,411 B2 | 8/2003 | Daoud et al. |
| 6,649,804 B2 * | 11/2003 | Eakin .......................... 602/56 |
| 6,653,520 B1 | 11/2003 | Mouton |
| 6,841,715 B2 * | 1/2005 | Roberts ....................... 602/54 |
| 7,119,247 B2 | 10/2006 | Worthley |
| 2002/0156410 A1 | 10/2002 | Lawry |
| 2002/0193723 A1 | 12/2002 | Batdorf, Sr. et al. |
| 2003/0040691 A1 | 2/2003 | Griesbach, III et al. |
| 2003/0059626 A1 | 3/2003 | Daoud |
| 2003/0088202 A1 | 5/2003 | Gilman |
| 2003/0120229 A1 | 6/2003 | de Jong et al. |
| 2003/0125654 A1 | 7/2003 | Malik |
| 2003/0167028 A1 | 9/2003 | Binder et al. |
| 2003/0194526 A1 | 10/2003 | Vesley et al. |
| 2003/0199800 A1 | 10/2003 | Levin |

FOREIGN PATENT DOCUMENTS

| | | |
|---|---|---|
| EP | 0160572 | 11/1985 |
| EP | 0106440 | 11/1987 |
| EP | 0413251 | 11/1994 |
| EP | 0799693 A2 | 10/1997 |
| EP | 1374813 A2 | 1/2004 |
| GB | 778813 | 7/1957 |
| GB | 898826 | 6/1962 |
| GB | 1280631 | 7/1972 |
| GB | 1398011 | 6/1975 |
| GB | 2061732 | 5/1981 |
| GB | 2074029 | 10/1981 |
| GB | 2093702 | 9/1982 |
| GB | 2093703 | 9/1982 |
| JP | 05069512 A | 3/1993 |
| WO | WO89/08555 | 9/1989 |
| WO | WO02062403 A1 | 8/2002 |
| WO | WO03026544 A1 | 4/2003 |
| WO | WO03043553 A1 | 5/2003 |

| | | | |
|---|---|---|---|
| WO | WO03045294 A1 | 6/2003 | |
| WO | WO03055536 A1 | 7/2003 | |
| WO | WO03057103 A1 | 7/2003 | |
| WO | WO03061538 A1 | 7/2003 | |
| WO | WO03061539 A1 | 7/2003 | |
| WO | WO03068283 A2 | 8/2003 | |
| WO | WO03086255 A1 | 10/2003 | |

OTHER PUBLICATIONS

"Silicone Gel Breast Implants", The report of the Independent Review Group, What is silicone?; downloaded on Jan. 27, 2005 at http://www.silicone-review.gov.uk/silicone/index.htm.

"Silicone Chemistry Overview", pp. 1-12, 1997, Dow Corning Corporation.

Bentley, David, "A Primer on How to Put Substrates Together" Paper, Film & Foil Converters, Downloaded on Jan. 27, 2005 at http://pffc-online.com/unprinted_rolls/paper_coatinglaminating/.

Perkins, K., et al., "Silicone gel: a new treatment for burn scars and contractures", Burns, vol. 9, No. 1.

Smith & Nephew—Cutinova Hydro downloaded on Apr. 29, 2004 at http://wound.smith-nephew.com/us/Standard.asp?NodeId=2608.

Krieser, Jason K., et al., "Comparison of Hydrophilic Polyurethane Foam Dressings", downloaded on Jun. 16, 2003, at http://woundcare.org/newsvol2n2/pr12.htm.

Moist Wound Healing, downloaded Jun. 16, 2003 at http://www.lawrenceville.org/_mgolden/moistwd.html.

Molnlycke Healt Care's Business Area Wound Care Global, Safetac technology, Silicone.

Molnlycke Healt Care's Business Area Wound Care Global, Safetac technology, Safetac technology.

Thomas, Steve, Ph.D., "Soft silicone dressings: frequently asked questions", World Wide Wounds, www.worldwidewounds.com/2003/october/Thomas/Soft-Silicone-FAQ.html.

Tendra, mepilex border.

Tendra Open Wound Care System, tendra mepilex transfer.

Thomas, David R., MD. "Prevention and treatment of pressure ulcers: What works? What doesn't?", Cleveland Clinic Journal of Medicine, vol. 68, No. 8, Aug. 2001, pp. 704-722.

Thomas, Steve, Ph.D., "Atraumatic dressings", World Wide Wounds, www.worldsidewounds.com/2003/january/thomas/atraumatic-dressings.html.

Tendra Open Wound Care System, mepilex border.

Versiva, Instructions for Use.

Versiva, "Innovative Moisture Management", downloaded Jan. 16, 2004 at http://www.convatec.com/versiva/us/three_proven_tech.htm.

Cica-Care, Instructions for Use, downloaded Nov. 13, 2002 at http://wound.smith-nephew.com/us/ProductDetail.asp?UniqueID=0%...

Smith & Nephew—Allevyn Adhesive, downloaded Jan. 16, 2004 at http://wound.smith-nephew.com/us/Product.asp?NodeID=452&UniqueID=0.9393...

Smith & Nephew—Allevyn Technology, downloaded Jan. 16, 2004 at http://wound.smith-nephew.com/us/Standard.asp?NodeID=2711&UniqueID=0.92594.

Donatas Satas, ed., Advances in Pressure Sensitive Adhesive Technology 2, pp. 724-746. 1995.

* cited by examiner

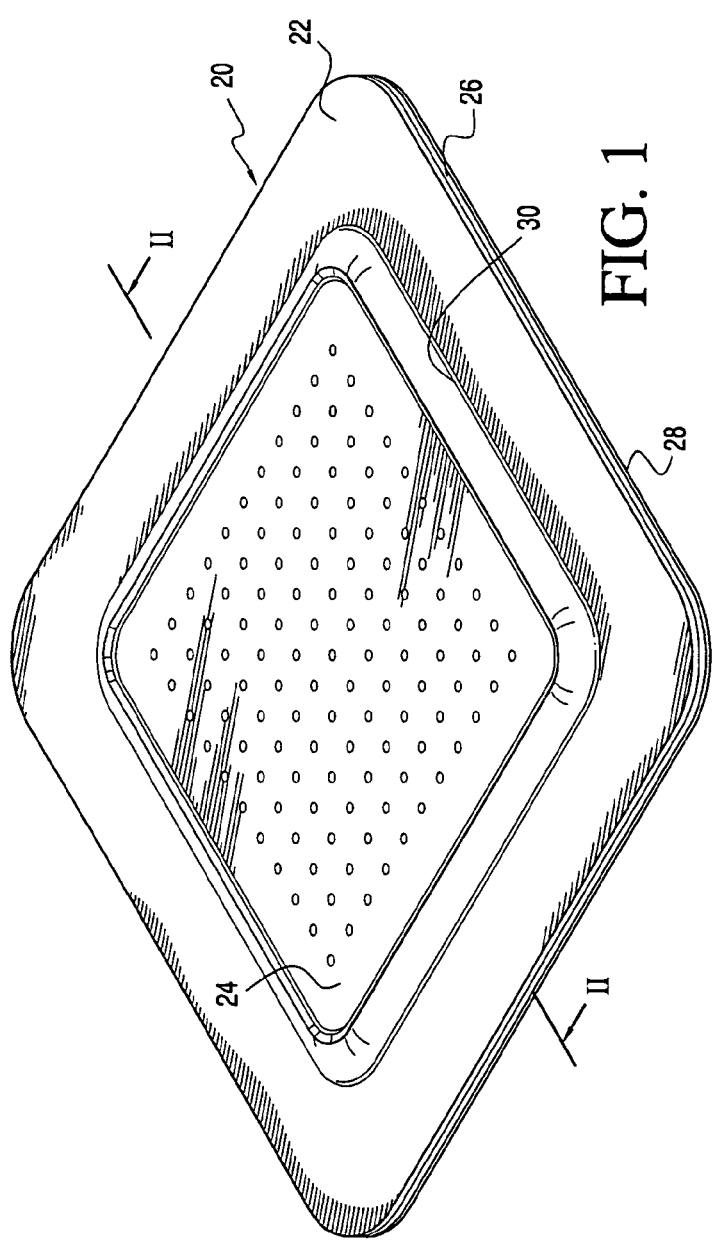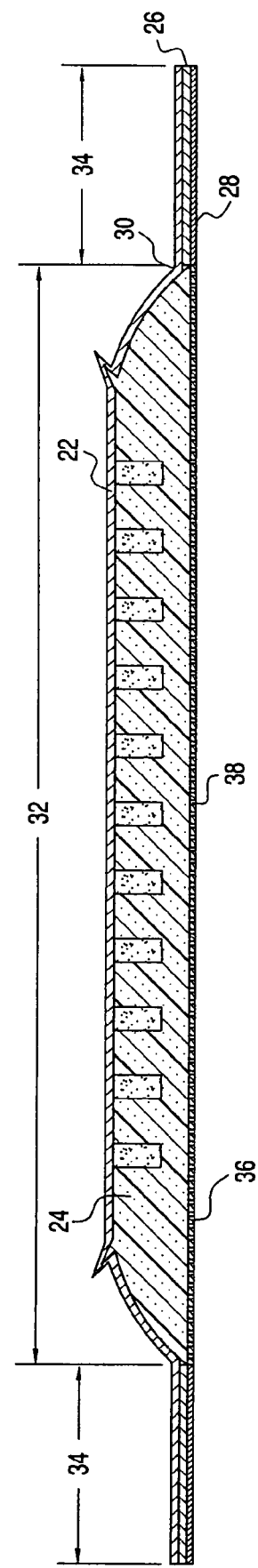
FIG. 1
FIG. 2

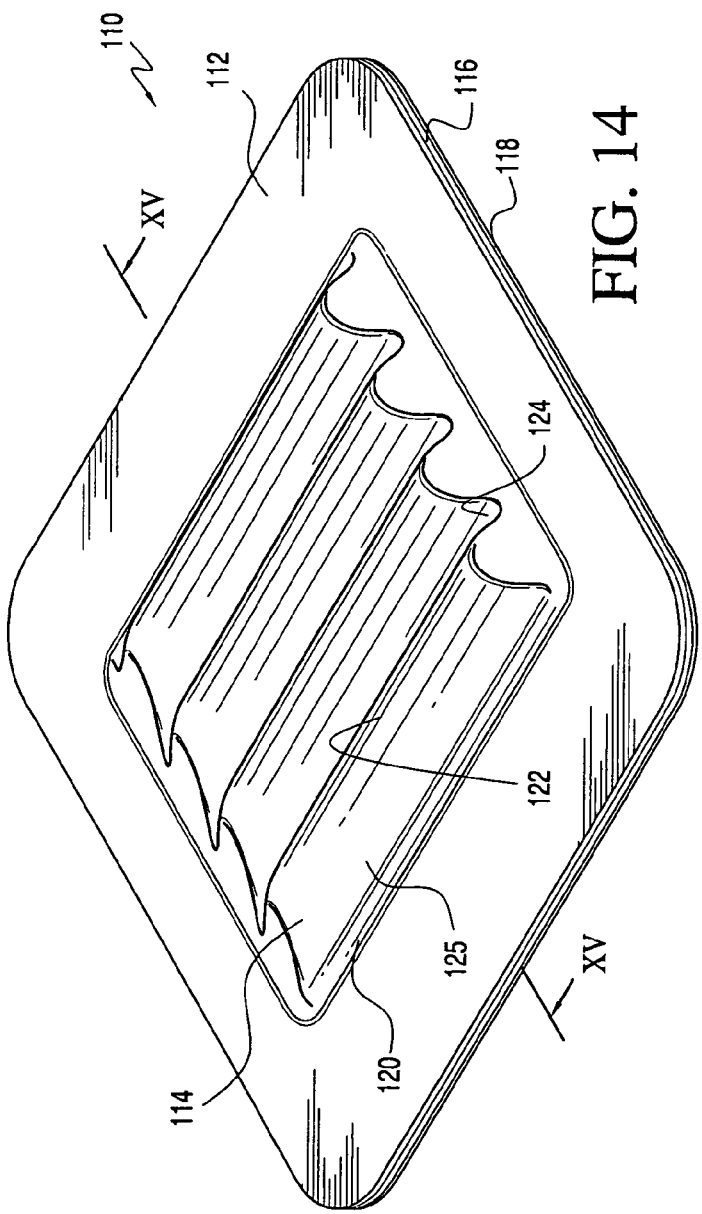
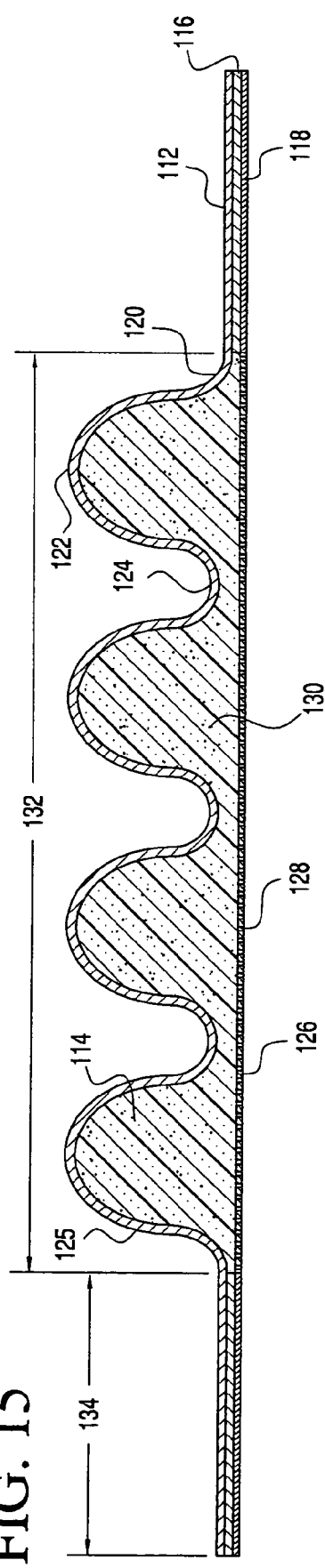
FIG. 14
FIG. 15

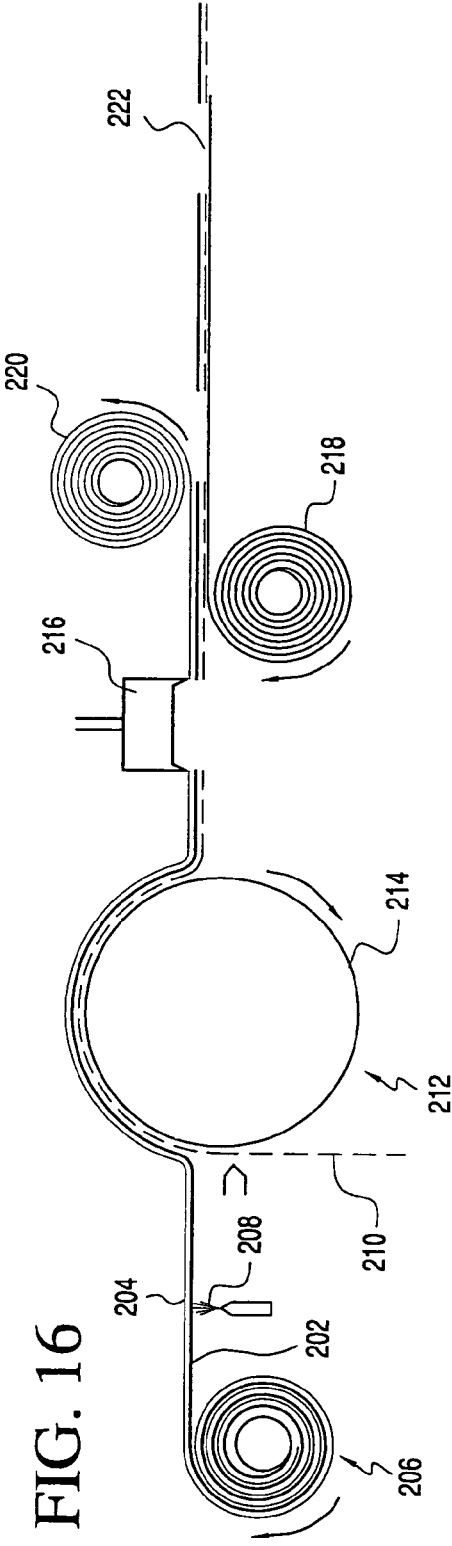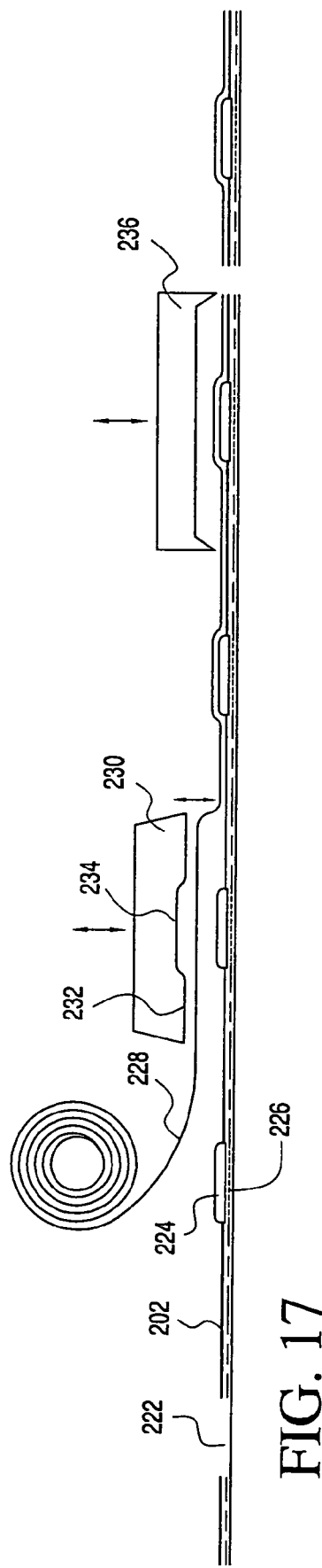

WOUND DRESSING AND METHOD FOR MANUFACTURING THE SAME

CROSS REFERENCE TO RELATED APPLICATIONS

This application is a divisional application of U.S. application Ser. No. 10/924,861 filed on Aug. 25, 2004 which claims the benefit of U.S. provisional application Nos. 60/503,546 filed Sep. 17, 2003, 60/518,317 filed Nov. 10, 2003, and 60/543,401 filed Feb. 11, 2004.

BACKGROUND

Historically, many diverse materials of various origins have been used to treat wounds by absorbing wound fluids and tissue, hereinafter generally referred to as exudate, from a wound site with some type of absorbent material. In recent years, use of polymeric-based wound care products have become increasingly popular to control wound site environmental factors such as water vapor, oxygen permeability, bacterial impermeability, and absorption of exudate. Such wound care products are tailored to meet specific requirements including conformability to a body portion, selective adherence to a wound bed, and adhesiveness to the skin surrounding the wound site.

Recently, occlusive or moisture-retentive dressings have gained increasing acceptance in treating wounds, in particular pressure sores and ulcers. A wide variety of types of structures are known in the art for use in or as occlusive dressings and generally comprise components for receiving, absorbing and retaining exudate. Typically, these wound care products include polymeric foams, polymeric films, particulate and fibrous polymers, hydrogels and hydrocolloids. Dressings with at least one of these components promote wound healing by providing a moist environment, while removing excess exudate and toxic components, and further serve as a barrier to protect the wound from secondary bacterial infection. While these known occlusive wound dressings can effectively manage a wound, many have been found to possess certain limitations or disadvantages.

Developments in the field of silicone manufacturing have led Ossur hf of Reykjavik, Iceland, and assignee of the present invention, to produce silicone products adapted for skin contact that provide superb softness, and gentle skin contact. In particular, such silicone manufacturing has led to advances in improved comfort and cushioning of prosthetic suspension liners that have excellent durability and intimacy using proprietary silicone technology of Ossur hf. It has been found that by applying the silicone technology of Ossur hf to produce a discrete ultra-thin, perforated tacky silicone sheet, a silicone adhesive layer can be produced that possesses superior gentle adherence to wound sites while not damaging skin and the wound bed due to single or repeated removal of the silicone layer.

While a wound dressing having an absorbent core with a silicone adhesive layer provides gentle adhesion to the wound and the surrounding skin, there are many instances where it is required that the wound dressing has greater tackiness in outer lying regions bordering the wound. Difficulties arise in that there must be a balance of gentle adhesion at the wound site and adjacent areas of skin so as to avoid disrupting the wound, while still providing sufficient adhesion of the dressing to accommodate movement of a patient or at wound sites difficult to maintain adhesion.

Efforts have been made to apply a wound dressing having a silicone adhesive layer with sufficient gentle adhesive properties to a wound and further secured to the outer lying skin by the application of medical tape over the wound dressing. While this has proven effective at maintaining a wound dressing on a patient's body, more time and care is required to apply the wound dressing. Furthermore, the adhesive on the medical tape may be too tacky and irritate the skin upon which it is applied during application and removal thereof.

Despite the ready availability of medical tape, it is desirable to provide a wound dressing that possesses the adherence capabilities of medical tape in a stand alone form yet gentle to the shin.

From a standpoint of ease of application and comfort to a patient, it is desirable that a wound dressing include different areas of adhesion, wherein an adhesive layer disposed on the absorbent core has gentle skin adherence while a portion of the wound dressing bordering the absorbent core has greater skin adherence. Thus, with such a wound dressing, the need for medical tape is mitigated and the wound dressing can be applied in a simpler fashion without discomfort to a patient.

For the foregoing reasons, there is a demand for an improved wound dressing which prevents wound trauma upon wound dressing changes, improves the durability and lifetime of the wound dressing, anatomically conforms to a wound, possesses improved fluid uptake, retention and removal properties, and can be securely maintained on a patient's body. It is thus desired to produce a wound dressing having an adhesive layer that does not possess the drawbacks of known adhesive layers, and instead, gently adheres and detaches from a wound site while providing superior fluid uptake. Moreover, there is a demand for a wound dressing that includes adhesive means having greater skin adherence than an adhesive layer disposed over a wound.

SUMMARY

The present invention is directed to an improved wound dressing possessing superior skin adherence capabilities. In an embodiment of the wound dressing, the dressing includes a backing layer defining opposed proximal and distal surfaces including a center portion and a border portion, and an absorbent core having proximal and distal surfaces. A carrier layer is secured to the proximal surface of the border portion of the backing layer and defines an opening that surrounds the center portion of the backing layer. A first skin adherent facing layer is secured to a proximal surface of the carrier layer and generally corresponds to the border portion of the backing layer. A distal surface of an absorbent core is secured to the proximal surface of the center portion of the backing layer and extends through the opening of the carrier layer. A second skin adherent facing layer is secured to a proximal surface of the absorbent core.

According to one embodiment, the first facing layer has greater skin adhesive properties than the second facing layer. In this embodiment, the second facing layer is a discrete layer of silicone gel having a plurality of through extending apertures arranged in a pattern. The first facing layer is an imperforate layer of silicone gel, and may be applied to the backing layer with or without the aforementioned carrier layer as a reinforcement element. An advantage to this embodiment is that the dressing can provide greater adhesion to outlying areas of a wound while still maintaining gentle contact to the wound itself. Moreover, by using a carrier layer, the border portion of the wound dressing is reinforced and can be placed onto skin in greater tension without tearing the backing layer.

According to yet another embodiment, the backing layer defines contoured peripheral edges wherein the absorbent core has corresponding contoured peripheral edges generally corresponding in shape to the contoured shape of the backing layer. In a variant of this embodiment, the peripheral edges of both the backing layer and absorbent core define a substantially non-linear profile. An advantage to this embodiment lies in that the wound dressing may be configured to be particularly applied to various body parts, thereby assuring greater adherence to skin and more aptly absorbing wound exudate. Due to the border portion of the dressing, this embodiment is advantageous since it is configured to respond to the movement of a body part, thereby reducing the likelihood of the dressing being pulled or loosening from the skin due to such movement.

According to yet another embodiment, the combination of the backing and carrier layers defines a plurality of pleats, and the center portion of the backing layer has a generally planar configuration. In a variant of this embodiment, the pleats generally taper from the peripheral outer edges of the backing layer to the boundary between the center portion and border portion of the backing layer. Similar to the contoured dressing embodiment, the pleats of this embodiment are advantageous in that they reduce the magnitude of tensile forces created in the border portion of the dressing in response to body movement, and thereby reduce the likelihood of the dressing being pulled or loosening from the skin due to such movement.

According to yet another embodiment, the backing and carrier layers define an undulating profile in the areas of the border portion of the dressing, and the central portion of the dressing is substantially planar. The corrugations are defined as parallel rows having a generally undulating form. This embodiment is advantageous in that the backing and carrier layers are stretchable over outlying areas of the wound and thereby provide greater tension of the dressing against the skin. Moreover, this embodiment accommodates movement and swelling of the wound area.

According to yet another embodiment of the dressing, the absorbent core has an undulating profile and the backing layer closely adheres to the distal surface of the absorbent core. In a variant of this embodiment, the dressing includes a plurality of discrete hydrophilic particles enmeshed in the absorbent core. Furthermore, the border portion in a variant of this dressing may remain in a substantially planar configuration. This embodiment is particularly advantageous when the dressing is to be placed on an exuding joint wound so as to accommodate for movement and swelling of the wound area itself while being secured to the outlying areas of the wound.

Also provided are methods of manufacturing the embodiments of the wound dressing of the invention. According to one method, the method for manufacturing a wound dressing comprises the steps of providing a carrier layer having first and second surfaces, applying a first skin adherent facing layer onto the carrier layer, removing a center portion of the carrier layer to define an opening in the carrier layer, inserting an absorbent core having first and second surfaces within the opening of the carrier layer and securing a first surface of the backing layer having first and second surfaces over the second surface of the absorbent core and the second surface of the carrier layer.

In conjunction with the methods of manufacturing the embodiments of the wound dressing, numerous methods may be employed to secure the backing layer to the carrier layer and the absorbent core. According to one method a platen is provided which has a generally planar border region and a recessed center region relative to the border region that generally corresponds to the shape of the absorbent core. The platen is heated to an elevated temperature sufficient to thermal bond the carrier and backing layers, and secures the backing layer to the absorbent core. The platen is subsequently urged against the second surface of the backing layer to generate pressure thereon, the pressure being sufficient to substantially cause thermal bonding of the backing and carrier layers. The platen is then removed from the second surface of the backing layer after the first surface of the backing layer has thermal bonded to the second surface of the carrier layer and a portion of the absorbent core.

BRIEF DESCRIPTION OF THE DRAWINGS

These and other features, aspects, and advantages of the present invention will become better understood with regard to the following description, appended claims, and accompanying drawings where:

FIG. 1 is perspective view showing an embodiment of a wound dressing;

FIG. 2 is a sectional view of the wound dressing in FIG. 1 taken along line II-II;

FIG. 14 is a perspective view of an embodiment of a wound dressing with an absorbent core with an undulating profile;

FIG. 15 is a sectional view of the wound dressing in FIG. 14 taken along line XV-XV;

FIG. 16 is a schematic view showing a process for making features of a wound dressing; and FIG. 17 is a schematic view showing a process for making features of a wound dressing.

DETAILED DESCRIPTION OF VARIOUS EMBODIMENTS

A. Overview

Figure 4:
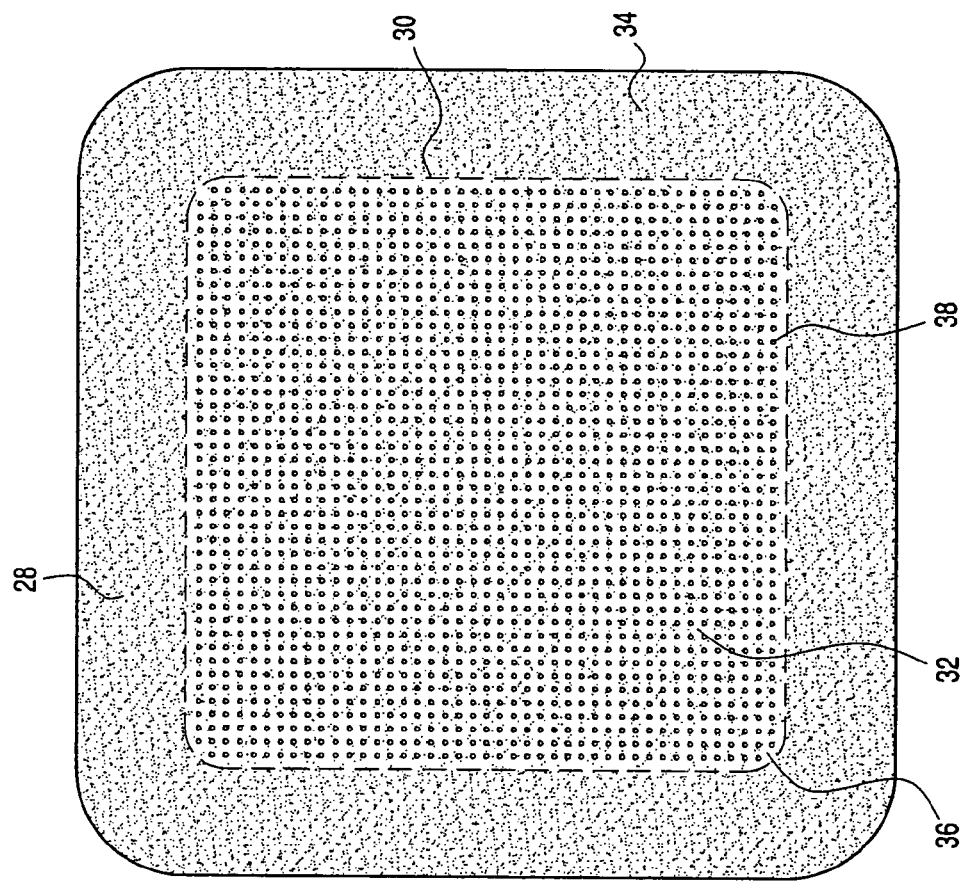
FIG. 4 is a bottom plan view of the wound dressing in FIG. 1.

A better understanding of different embodiments of the invention may be had from the following description read in conjunction with the accompanying drawings in which like reference characters refer to like elements.

While the disclosure is susceptible to various modifications and alternative constructions, certain illustrative embodiments thereof are shown in the drawings and will be described below in detail. It should be understood, however, that there is no intention to limit the disclosure to the specific embodiments disclosed, but on the contrary, the intention is to cover all modifications, alternative constructions, combinations, and equivalents falling within the spirit and scope of the disclosure and defined by the appended claims.

It will be understood that, unless a term is expressly defined in this patent to possess a described meaning, there is no intent to limit the meaning of such term, either expressly or indirectly, beyond its plain or ordinary meaning.

Any element in a claim that does not explicitly state "means for" performing a specified function, or "step for" performing a specific function, is not to be interpreted as a "means" or "step" clause as specified in 35 U.S.C. §112, paragraph 6.

B. Environment and Context of Embodiments

Various embodiments of the invention are provided to variously be used to absorb exudate, combat odor and infection, relieve pain, wound cleanse and maintain a moist environment at a wound surface to facilitate healing of the wound. The embodiments of the invention are particularly configured to absorb exudate or wound fluid and may therefore be suitable for application for a variety of different wound types.

The various embodiments are conformable to a variety of locations on a living body, and may be dimensioned to accommodate different types and sizes of wounds. Moreover, the adhesive properties may be modified according to the location and type of wound to be treated while taking into consideration the potential for the dressing to cause sensitivity reactions, the ease of application and removal including the production of pain and trauma to wound surfaces, and the interval between wound dressing changes.

Thus, it is to be clearly understood that the various embodiments of the wound dressing according to the invention may be made in any desired sizes and shapes for use over any afflicted portion of a human or other living body.

While features are shown in the drawing figures that are not described in detail in the description that follows, a detailed description of such features may be found in application Ser. No. 10/725,574 that is incorporated herein by reference.

C. Various Embodiments of the Wound Dressing

As shown in FIG. 1, an embodiment of a wound dressing 20 includes a liquid impervious, vapor permeable backing layer 22 having proximal (first) and distal (second) surfaces. The backing layer 22 defines a center portion 32, and a border portion 34 surrounding the center portion 32. A carrier layer 26 is provided which has proximal and distal surfaces wherein the distal surface of the carrier layer 26 is secured to the proximal surface of the border portion 34 of the backing layer 22 and borders the center portion 32. A first skin adherent facing layer 28 is secured to the proximal side of the carrier layer 26.

The carrier layer 26 defines an opening corresponding to the center portion 32 of the backing layer 22, and substantially outlines the border portion 34.

Figure 3:
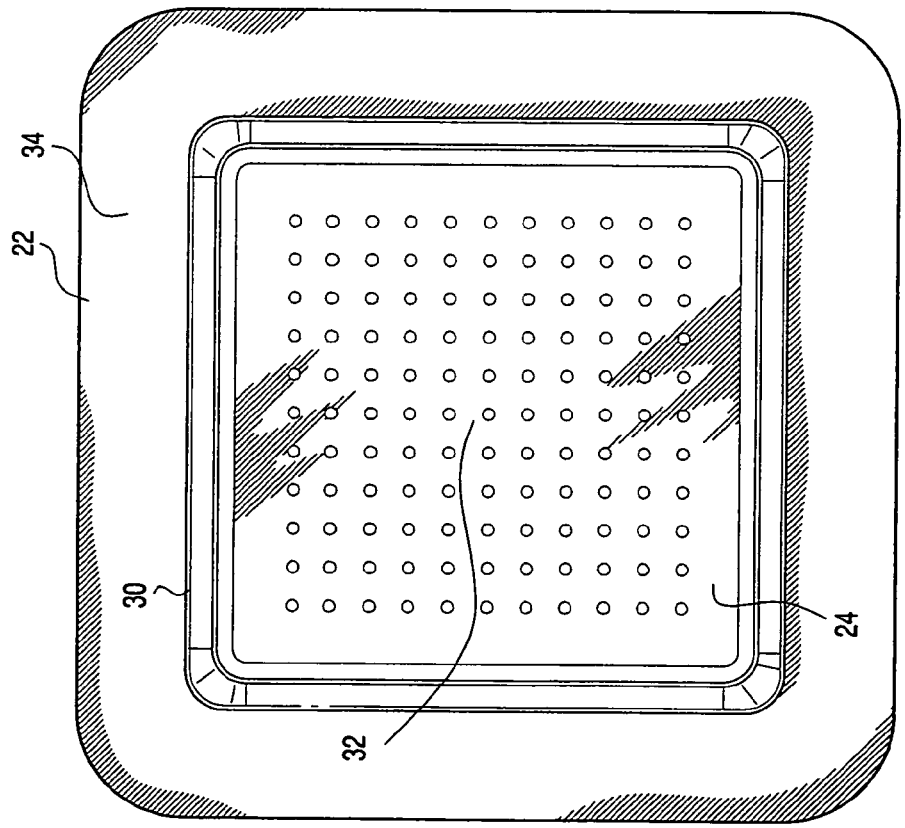
FIG. 3 is a top plan view of the wound dressing in FIG. 1.

As exemplified in FIGS. 2 and 3, an absorbent core 24 is secured to the proximal surface of the center portion 32 of the backing layer 22. The absorbent core 24 is positioned on the backing layer 22 such that the absorbent core 24 extends through the opening of the carrier layer 26. A second skin adherent facing layer 36 is disposed along a proximal surface of the absorbent core 24. According to this embodiment, the first facing layer 28 has greater skin adherence properties than the second facing layer 36.

In the embodiment shown in FIGS. 1-4, the backing layer 22 is thermal bonded to the carrier layer 26, and at least portions of the backing layer 22 are secured to the distal surface of the absorbent core 24. Moreover, the backing layer 22 may be thermal bonded to the absorbent core 24 at a boundary region 30 near or at the peripheral edges of the proximal surface thereof By thermal bonding the absorbent core 24 to the backing layer 22, a seal may be formed along the regions of bonding. A bevel may also be defined near the peripheral edges of the absorbent core to gradually reduce stresses of the absorbent core as it absorbs wound exudate and to minimize imprints on skin of a wearer.

It will be understood that the backing layer may be secured to the carrier layer and the absorbent core in any manner known to one skilled in the art of wound dressings, and any such methods are within the scope of this application. Such other methods include using an adhesive, pressure molding, or mechanical fixation with elements such as stitches, pins or staples.

Preferably, the first facing layer 28 is a silicone gel coated onto the carrier layer 26, and the second facing layer 36 is a discrete sheet of silicone gel directly secured to the absorbent core 24. As shown more fully in FIG. 4, the second facing layer 36 includes a plurality of apertures 38 that are preferably arranged in a predetermined pattern such that they are equally spaced from one another and possess a generally uniform size and shape.

While the first facing layer 28 is shown in FIG. 4 as not including apertures, the first facing layer 28 may be configured to include a plurality of apertures in a similar formation as those described above in reference to the second facing layer 36. Furthermore, alternative embodiments regarding the pattern, configuration and dimension of the apertures of the facing layers is provided in application Ser. No. 10/725,574.

Figure 5:
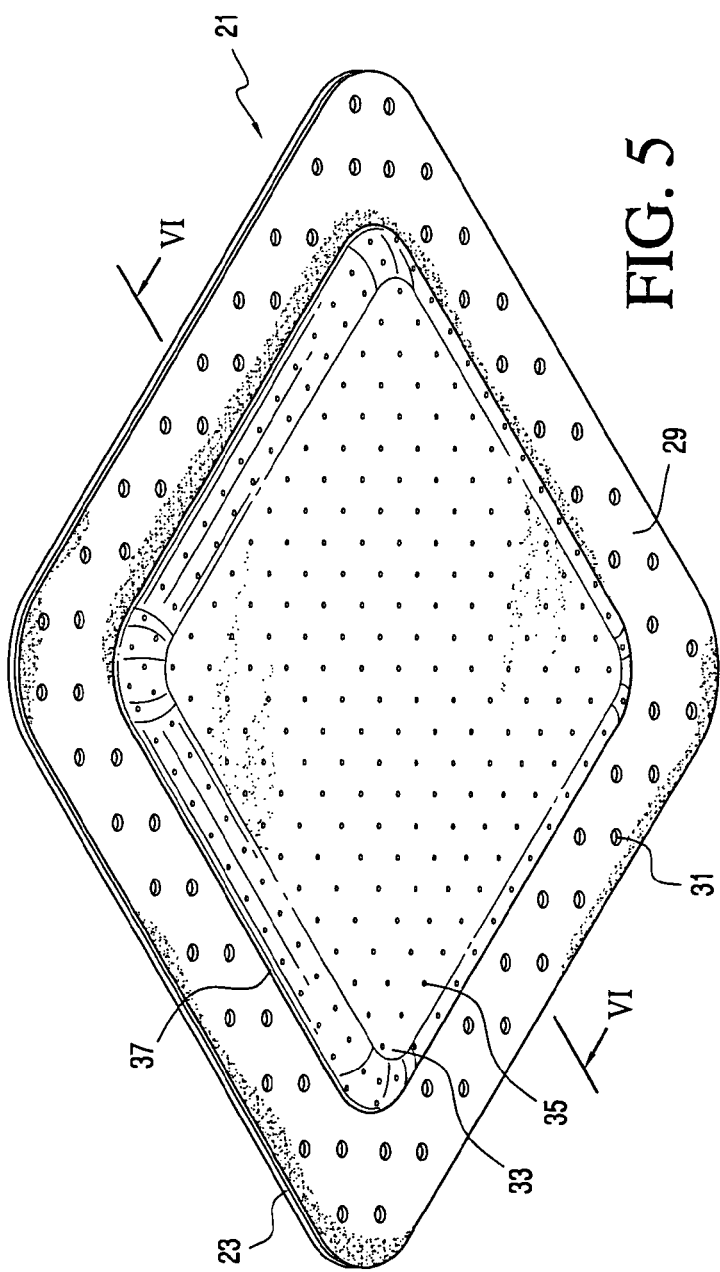
FIG. 5 is a bottom plan view of an embodiment of a wound dressing.
Figure 6:
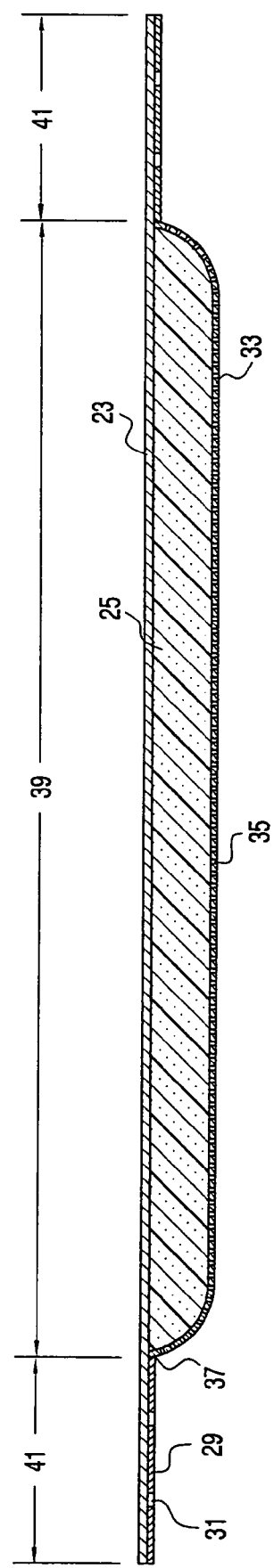
FIG. 6 is a sectional view of the wound dressing in FIG. 5 taken along line VI-VI.

FIGS. 5 and 6 show another embodiment of the wound dressing including a backing layer 23 having proximal and distal surfaces. The backing layer defines a center portion 39 and a border portion 41 surrounding the center portion 39. A first skin adherent facing layer 29 is secured to the proximal surface of the backing layer 23. The first facing layer 29 defines a plurality of apertures 31.

A substantially planar distal surface of an absorbent core 25 is secured to the proximal surface of the center portion 39 of the backing layer 23. A second skin adherent facing layer 31 is secured to a proximal surface of the absorbent core 25. The second facing layer 31 defines a plurality of apertures 25 arranged in a pattern. A boundary 37 delimits the first and second facing layers 29, 31, and distinguishes the center and border portions 39, 41 of the dressing.

Figure 7:
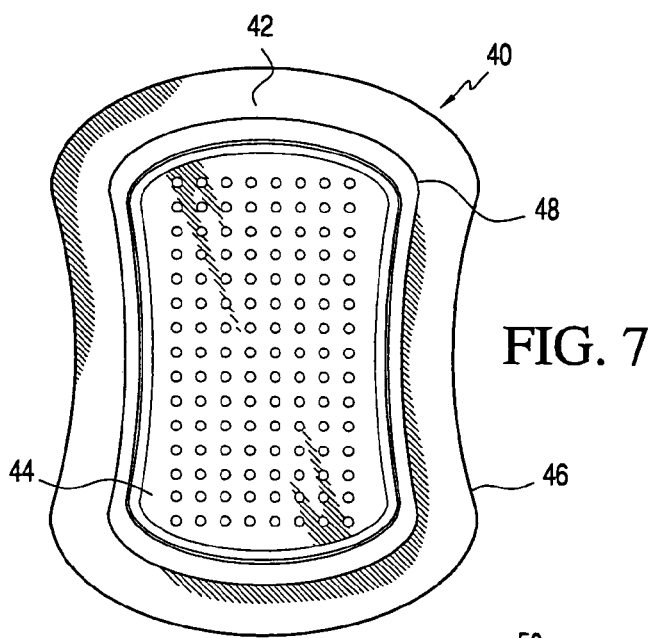
FIG. 7 is a top plan view of an embodiment of a wound dressing having contoured peripheral edges.
Figure 8:
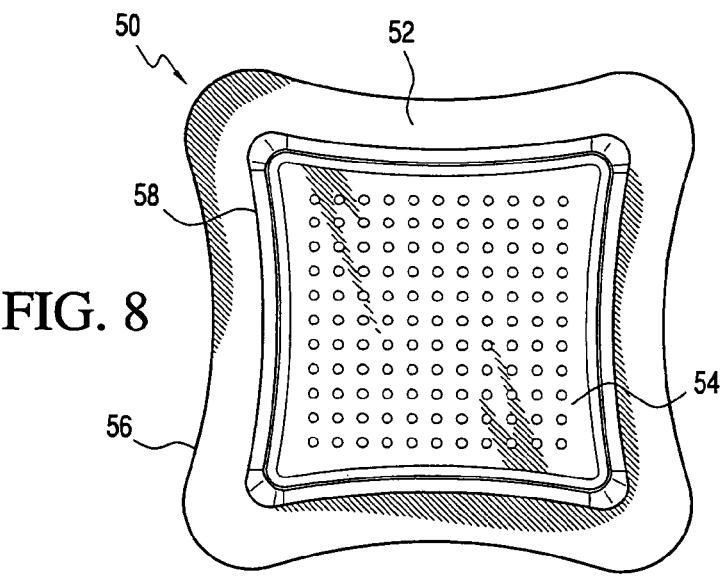
FIG. 8 is a top plan view of an embodiment of a wound dressing having contoured peripheral edges.
Figure 9:
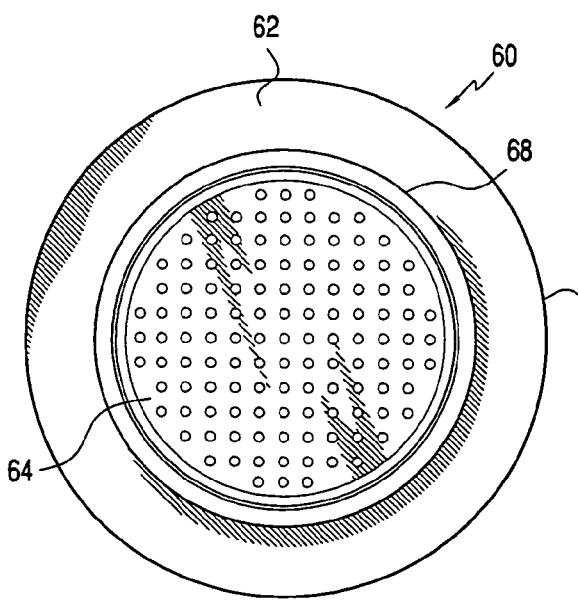
FIG. 9 is a top plan view of an embodiment of a wound dressing having contoured peripheral edges.

In addition to the basic footprint or configuration of the wound dressing exemplified in FIGS. 1-4, other configurations are possible and are fully within the scope of the present invention. FIGS. 7-9 show exemplary wound dressing embodiments generally having the same backing layer and absorbent core relationship as in the wound dressing of FIG. 1. In each of the embodiments, the backing layer defines contoured outer edges and the absorbent core has contoured outer edges generally corresponding in shape to the contoured outer edges of the backing layer.

FIG. 7 illustrates a dressing 40 having a backing layer 42 and an absorbent core 44 each with a generally elongate profile such that the outer edges 46, 48 of both the backing layer 42 and the absorbent core 44 are concave and convex at certain portions thereof. FIG. 8 shows another embodiment of a dressing 50 wherein a backing layer 52 and an absorbent core 54 each have generally equal length outer sides 56, 58 that are both concave and convex. FIG. 9 shows yet another embodiment of a dressing 60 wherein the backing layer 62 and the absorbent core 64 have peripheral edges 66, 68 that are generally circular and concentric with one another.

Figure 10:
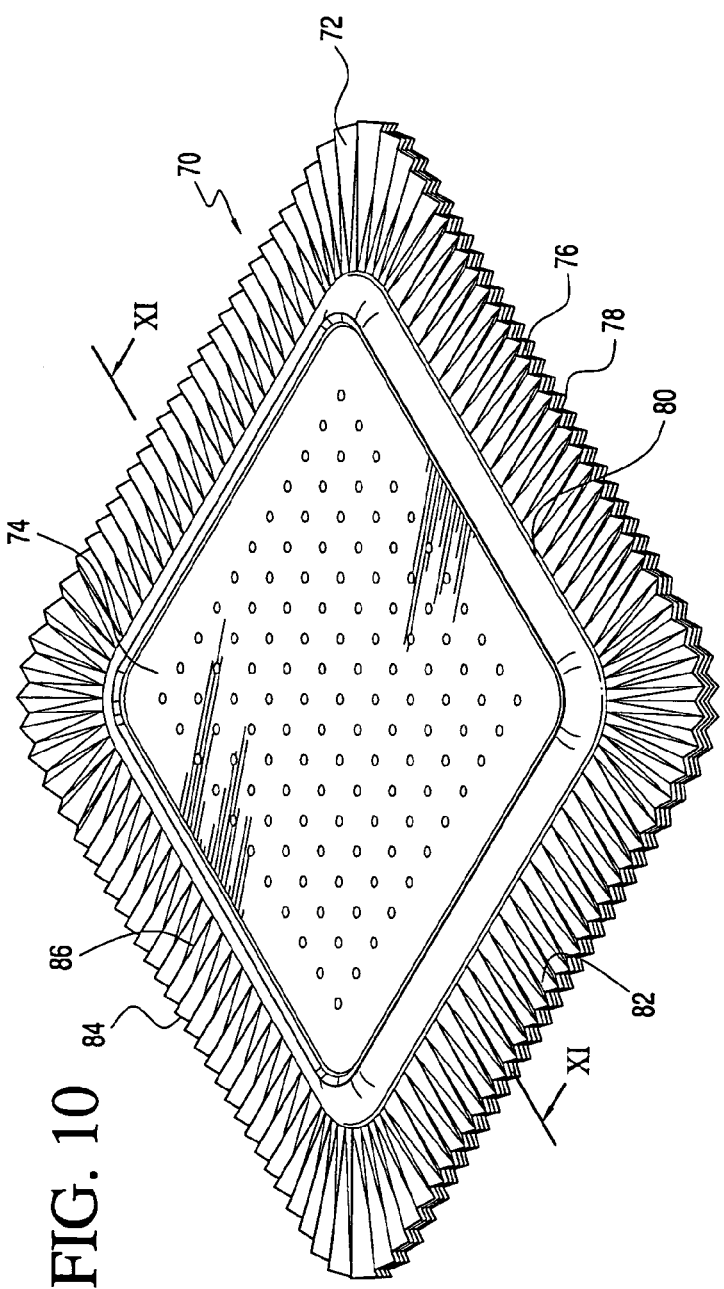
FIG. 10 is a perspective view of an embodiment of a wound dressing having a pleated border portion.
Figure 11:
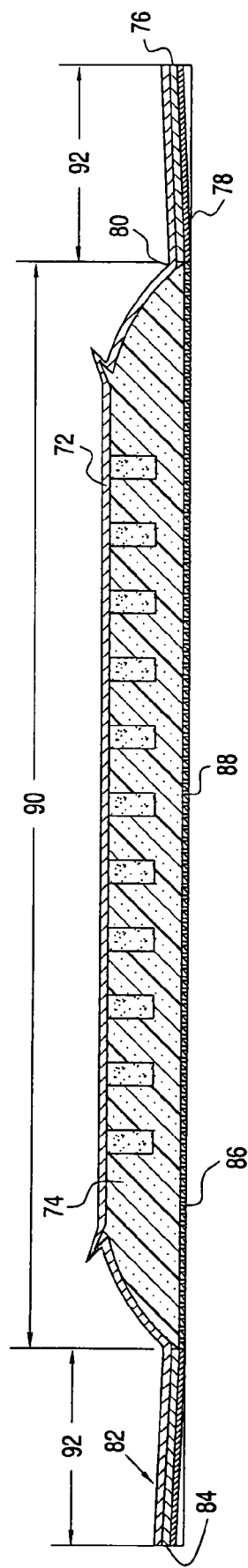
FIG. 11 is a sectional view of the wound dressing in FIG. 10 taken along line XI-XI.

Turning to FIGS. 10 and 11, another embodiment of a wound dressing 70 is shown having a center portion 90 and a border portion 92. In the dressing 70, a proximal surface of a backing layer 72 is secured to a distal surface of an absorbent core 74 wherein a boundary 80 generally defined as the peripheral edges of the absorbent core 74 delimits the center portion 90 and border portion 92 of the dressing 70. A distal surface of a carrier layer 76 is secured to the proximal surface of the backing layer 72 and has an opening that generally surrounds the absorbent core 74, whereby the carrier layer 76 is associated with the border portion 92 and the absorbent core 74 is associated with the center portion 90 of the dressing 70. A first facing layer 78 is secured to the proximal surface of the carrier layer 76. A second facing layer 86 is secured to the proximal surface of the absorbent core 74 and defines a plurality of apertures 88.

In observing FIG. 11, the border portion 92 of the backing layer 72 defines a plurality of pleats 82 that extend from the peripheral edge 84 of the backing layer 72, and have a taper 86 that leads from the edge 84 towards the boundary 80. The pleats 82 are generally arranged around the border portion 92 of the dressing 70 and extend towards the center portion 90. The pleats 82 are equally formed by the carrier layer 76 and the first facing layer 78 as these layers generally follow the contours of the backing layer 72 within the border portion 92 thereof.

According to variations of this embodiment, the pleats may not include a taper and, moreover, the backing layer may comprise at least two discrete portions whereby each portion corresponds to a center portion and a border portion of the dressing. Such two backing layer portions may be joined at the boundary between the center and border portions of the dressing.

Figure 12:
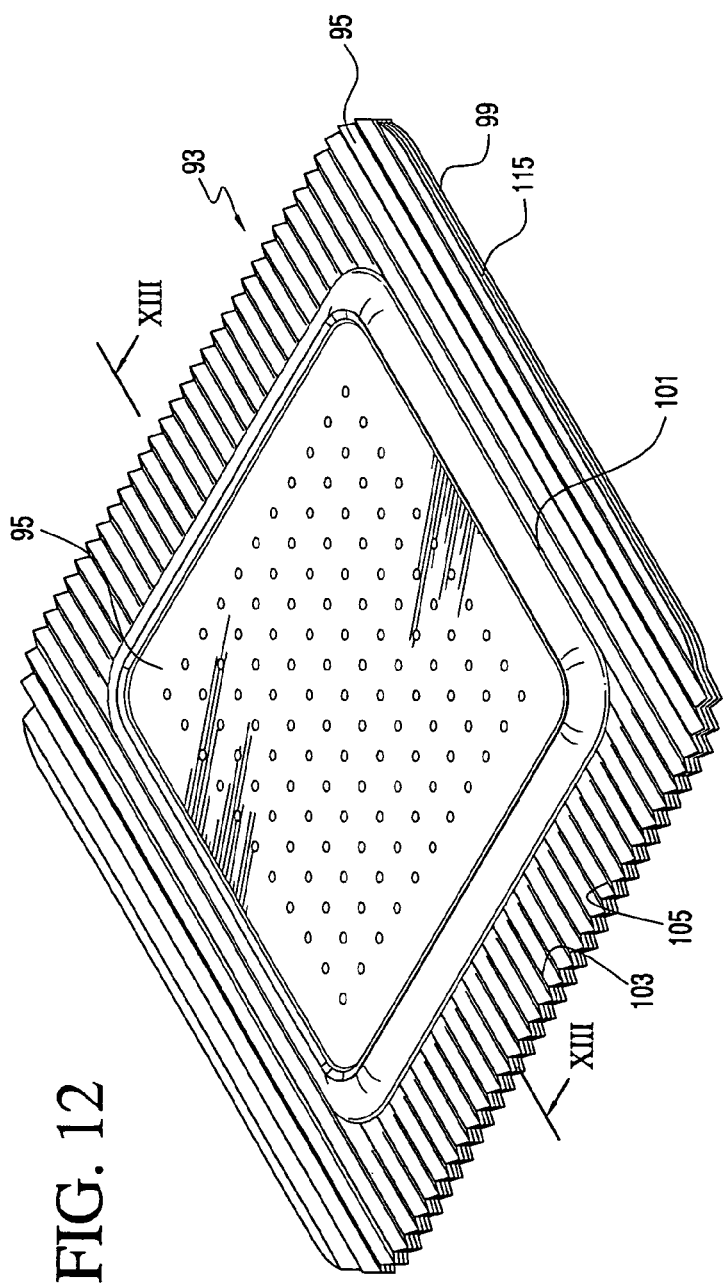
FIG. 12 is a perspective view of an embodiment of a wound dressing having a border portion with an undulating profile.
Figure 13:
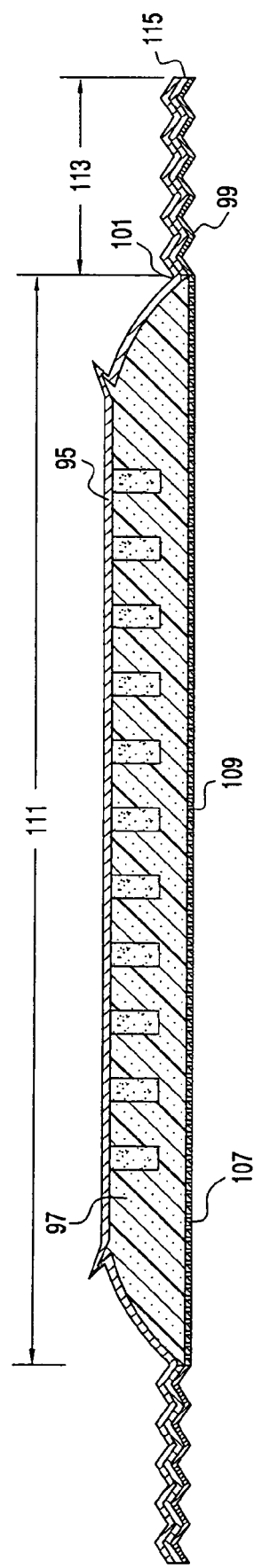
FIG. 13 is a sectional view of the wound dressing in FIG. 12 taken along line XIII-XIII.

As illustrated in FIGS. 12 and 13, another embodiment of a wound dressing 93 is shown having a center portion 111 and a border portion 113. In the dressing 93, a proximal surface of a backing layer 95 is secured to a distal surface of an absorbent core 97 wherein a boundary 101 generally defined as the peripheral edges of the absorbent core 97 delimits the center and border portions 111, 113 of the dressing 93. A distal surface of a carrier layer 97 is secured to the proximal surface of the backing layer 95 and has an opening that generally surrounds the absorbent core 95, whereby the carrier layer 97 is associated with the border portion 113 and the absorbent core 97 is associated with the center portion 111 of the dressing 93. A first facing layer 99 is secured to the proximal surface of the carrier layer 95. A second facing layer 107 is secured to the proximal surface of the absorbent core 97 and defines a plurality of apertures 109.

In observing FIG. 13, the border portion 113 of the backing layer 95 has an undulating profile comprising alternating ridges 103 and grooves 105. In this embodiment, the ridges 103 and grooves are generally in a parallel arrangement and laterally extend across the width of the dressing 93. The ridges 103 and grooves 105 are equally formed by the carrier layer 97 and the first facing layer 99, and these layers generally follow the contours of the backing layer 95 within the border portion 113 of the dressing 93.

According to variations of this embodiment, the undulating profile may extend across or in portions along the border and center portions of the dressing. Moreover, the pitch and depth of the ridges and grooves may be modified as deemed necessary to provide capabilities such as a desired stretchability of the dressing. Moreover, the cross-section of the ridges and grooves may also be modified as considered necessary to provide optimum stretchability, absorbency and skin adhesion.

As illustrated in FIGS. 14 and 15, another embodiment of a wound dressing 110 is shown having a center portion 132 and a border portion 134. In the dressing 110, a proximal surface of a backing layer 112 is secured to a distal surface of an absorbent core 114 wherein a boundary 120 generally defined as the peripheral edges of the absorbent core 114 delimits the center and border portions 132, 134 of the dressing 110. A distal surface of a carrier layer 116 is secured to the proximal surface of the backing layer 112 and has an opening that generally surrounds the absorbent core 114, whereby the carrier layer 116 is associated with the border portion 134 and the absorbent core 114 is associated with the center portion 132 of the dressing 110. A first facing layer 118 is secured to the proximal surface of the carrier layer 116. A second facing layer 126 is secured to the proximal surface of the absorbent core 114 and defines a plurality of apertures 128.

In observing FIG. 15, the absorbent core 114 has an undulating profile comprising of alternating ridges 122 and grooves 124. In this embodiment, the ridges 122 and grooves 124 are generally in a parallel arrangement and laterally extend across the width of the absorbent core 114. As shown, the side portion 125 of the ridges 122 and grooves 124 is generally tapered to provide features such as greater conformability and absorption. The absorbent core 114 includes a plurality of hydrophilic particles 130 enmeshed therein, as explained in greater detail in application Ser. No. 10/725,574.

Variations of the embodiment shown in FIGS. 14 and 15 are possible in that the undulating profile may be modified according to a desirable configuration. For example, the ridges and grooves may be increased or decreased, and the cross-sectional profile of the ridges and grooves can be modified as considered necessary to provide features such as improved stretchability, absorbency and skin adherence.

The facing layers used in each of the embodiments of the present invention are preferably liquid and moisture impervious layers that are bonded to the proximal surface of either the carrier layer or absorbent core. In a preferred embodiment, the facing layers comprise a cross-linked silicone elastomer gel, such as, for example, a cross-linked silicone (polydimethyl siloxane gel) manufactured by NuSil Technology (Carpenteria, Calif.) under product designations MED-6340 or MED-6345 which is tackier than MED-6340. Preferably, the first facing layer comprises silicone gel under product designation MED-6345 and the second facing layer comprises silicone gel under product designation MED-6340.

According to a preferred embodiment, the method used to evaluate adhesion between the different facing layers includes measuring the force required to peel a 25 mm wide sample comprising a silicone gel layer from a stainless steel plate. The differences in the force (measured in N/25 mm) used to remove the sample indicate the difference in the skin adhesion. In the embodiments of the facing layers described herein, the adhesion level on stainless steel of the facing layers are as follows: border portion (first facing layer: 1-3 N/25 mm) and center portion (second facing layer: 0.01-0.03 N/25 mm). It will be noted, however, that the adhesion levels described herein are only exemplary and may be modified according to desired adhesion levels.

In alternative variations, the facing layers may comprise a pressure sensitive adhesive known to those skilled in the art of adhesives and wound dressings and described in application Ser. No. 10/725,574. Moreover, the first facing layer may be provided with or without apertures, such as those defined by the second facing layer in each of the embodiments particularly described herein.

The facing layers preferably have a thickness in the range of 0.05 mm to 0.5 mm, and more preferably 0.1 mm. The conformability of the dressing to the wound is somewhat dependent on thickness of the components, such that when the dressing is applied to a body portion, it conforms to the surface even when the surface is moved. When the surface is flexed and then returned to an un-flexed position, the facing layer stretches to accommodate the flexation of the joint but is resilient enough to continue to conform to the surface when the surface is returned to its unflexed condition.

The various embodiments described herein using backing and carrier layers comprise a thin polymeric elastic or flexible film coating providing a bacterial barrier formed from a water vapor permeable pliable elastomer material. The film is continuous in that it has no perforations or pores which extend through the thickness of the film. Films of this type are known and generally are hydrophilic polymeric materials through which water vapor is capable of diffusing.

The backing layer is bonded to the distal surface of the absorbent core, and in a preferred embodiment, the backing layer is bonded only to the distal surface of the absorbent core and does not penetrate any pores, cells or cavities therein. Generally, the film used for the backing and carrier layers is 15 to 45 micrometers in thickness, with a preferred thickness of about 30 micrometers for the backing layer. For the carrier layer, the film may have the same thickness as in the backing layer. It is preferred, however, that the carrier layer possess a greater stiffness than the backing layer so as to provide greater control of applying the border portion of the dressing on skin and preventing curling, wrinkling or sticking of parts of the first facing layer to each other upon repeated application and removal of the dressing.

The backing layer may comprise polyurethane, such as a polyurethane film available from InteliCoat Technologies (South Hadley, Mass.) under product designation INSPIRE, elastomeric polyester, blends of polyurethane and polyester, polyvinyl chloride, and polyether-amide block copolymer. The preferred backing layer for use in the embodiments described herein is a polyurethane film since it exhibits a resilient property that allows the film to have good conformability and further has a high degree of stretchability.

The backing layer may be at least translucent, or sufficiently transparent so that the wound site to which the dressing is applied can be viewed through the dressing. It is advantageous to view the wound and healing thereof without removal of the dressing so as to avoid unnecessary handling of the dressing and exposure of the wound to the environment, and to reduce the likelihood of contamination.

The preferred carrier layer is a polyurethane film (such as Inspire 2301 from InteliCoat Technologies) that can be thermal bonded to the backing layer. Alternatively, other films, foams and mesh substrates may be employed that can be thermal bonded to the backing layer, or secured to the backing layer by other methods including the use of adhesives, stitching, pins, and staples. Preferably, the carrier layer should be sufficiently stiff so as to reinforce the border portion of the backing layer.

Suitable continuous conformable backing layers have a moisture vapor transmission rate (MVTR) of the backing layer alone of 1500 to 14600 g/m^2/24 hrs, preferably 2500 to 2700 g/m^2/24 hrs at 38° C. The backing layer thickness is preferably in the range of 10 to 1000 micrometers, more preferably 100 to 500 micrometers.

Suitable continuous conformable carrier layers have a moisture vapor transmission rate (MVTR) of the carrier layer alone of 1,000 to 30,000 g/m^2/24 hrs, preferably 14,000 g/m^2/24 hrs at 38° C. The carrier layer thickness is preferably in the range of 20-100 micrometers, more preferably 80 micrometers.

The absorbent core may be selected from a variety of different types known within the art of wound dressings, and the construction thereof may be configured in a variety of different arrangements as discussed more fully in application Ser. No. 10/725,574.

Numerous methods of manufacturing may be employed to make the embodiments of the wound dressing described herein. According to one method exemplified in FIGS. 16 and 17, the method for manufacturing a wound dressing comprises the steps of providing a carrier layer 202 having removable paper 204 thereon dispensed from a carrier layer roll 206. The carrier layer 202 is transported and a surface treatment substance 208 is applied on a proximal surface of the carrier layer 202. Preferably, the substance 208 is permitted to remain on the carrier layer 202 for approximately 30 minutes and maintained at 25° C. prior to the next step of the method to allow for any solvents in the primer to evaporate.

A suitable surface treatment substance includes silicone primers, such as those discussed more fully in application Ser. No. 10/725,574.

Next, a layer of an uncured silicone gel 210 is extruded onto the proximal surface of the carrier layer 202 over the substance 208. The carrier layer 202 with the uncured silicone gel layer 210 is transported over a drum 212 having a surface temperature of approximately 130° C. and maintained on the drum 212 for approximately 20 minutes. The drum 212 may be coated with any suitable release agent, such as Teflon, that will prevent adherence of the silicone gel 210 after curing thereof.

After the silicone gel layer 210 has cured and the carrier layer 202 is removed from the drum 212, a die cutter 216 is used to remove a center portion from the carrier layer 202. The removal of a center portion of the carrier layer 202 effectively forms an opening 222 through the carrier layer 202 and the cured silicone gel layer 210. Subsequently, the carrier layer paper 204 is removed from the distal surface of the carrier layer 202 onto a roll 220. A release paper or film 218 is applied to the proximal surface of the silicone gel layer 210.

As shown in FIG. 17, an absorbent core 224 is inserted within the opening 222 of the carrier layer 202 and the layer of silicone gel 210. A second facing layer 226 is provided on a proximal surface of the absorbent core 224. The second facing layer 226 is preferably an apertured discrete layer of silicone gel. Methods for making the apertured second facing layer 226 are discussed more fully in application Ser. No. 10/725,574.

According to the method exemplified in FIG. 17, a backing layer 228 is disposed over the distal surfaces of the carrier layer 202 and absorbent core 224. A platen 230 is provided as having a generally planar border region 232 and a recessed center region 234 relative to the planar border region 232 that generally corresponds to the shape of the absorbent core 224. The platen 230 is preferably heated to an elevated temperature suitable to thermal bond the backing layer 228 and the carrier layer 202 to one another and secure the absorbent core 224 thereon.

The platen 230 is urged against the distal surface of the backing layer 228 to generate pressure thereon sufficient to substantially cause thermal bonding of the backing layer 228 to the carrier layer 202. After a period of time sufficient to thermal bond the backing layer 228 to the carrier layer 202 and to at least portions of the absorbent core 224, the platen 230 is removed from the distal surface of the backing layer 228.

Subsequent to the thermal bonding of the backing layer 228 to the carrier layer 202 and the absorbent core 224, the wound dressing is cut to size with a die cutter 236.

In variations of the described method, the platen 230 may be modified to impart the pleated or undulating profile of the embodiments of the wound dressing described herein. Alternatively, other platen systems may be used after the backing layer is secured to the carrier layer that has the pleated or undulating profiles. Such platen systems may include mutually opposed platens having the impression of the different bordered profiles described herein, and which are suitably heated to impart the aforementioned bordered profiles.

Suitable platens or die cutters may be employed that impart the undulating profile of the absorbent core described herein. Moreover, the undulating profile may be formed by methods including cutting the absorbent core, forming the absorbent core, and molding the absorbent core in the configuration described herein. Such configuration of the absorbent core is preferably achieved prior to the application of the backing layer. Moreover, the impregnation of the hydrophilic particles in the absorbent core may be accomplished as discussed more fully in application Ser. No. 10/725,574, and is performed prior to the application of the backing layer.

Methods for applying the apertured facing layer onto the absorbent core are described more fully in application Ser. No. 10/725,574.

It will be understood that the above described embodiments and methods are illustrative in nature, and that modifications thereof may occur to those skilled in the art. Accordingly, this invention is not to be regarded as limited to the embodiments disclosed herein, but is to be limited only as defined in the appended claims.

We claim:
1. A wound dressing, comprising:
   a backing layer having first and second surfaces, the backing layer defining a center portion and a border portion surrounding the center portion;
   a first skin adherent facing section secured to the border portion of the backing layer along the first surface thereof;
   an absorbent core having first and second surfaces, the second surface of the absorbent core connected to the first surface of the backing layer within the center portion thereof; and
   a second skin adherent silicone-based facing layer directly bonded to the first surface of the absorbent core, the first facing section having greater skin adherence properties than the second facing layer, the first facing section and second skin adherent layer are co-planar and continuously form a bodyside surface of the wound dressing;
   wherein the absorbent core defines an undulating profile and the center portion of the backing layer generally follows the profile of the absorbent core
   wherein the first skin adherent facing section comprises a carrier layer having first and second surfaces, the second surface of the carrier layer secured to the first surface of the border portion of the backing layer, the carrier layer defining an opening generally corresponding to the center portion of the backing layer, the carrier layer is stiffer than the backing layer and the second surface of the carrier layer is thermally bonded to the first surface of the backing layer; and
   a first hydrophobic gel layer disposed along the first surface of the carrier layer.

2. The wound dressing according to claim 1, further comprising a plurality of discrete hydrophilic particles disposed in the absorbent core.

3. The wound dressing according to claim 2, wherein the absorbent core is hydrophilic foam.

4. The wound dressing according to claim 1, wherein the border portion of the backing layer is substantially planar.

5. The wound dressing according to claim 1, wherein the border portion of the backing layer defines a plurality of corrugations.

* * * * *